(12) United States Patent
Christie et al.

(10) Patent No.: US 7,785,328 B2
(45) Date of Patent: Aug. 31, 2010

(54) MINIMALLY INVASIVE BONE MILLER APPARATUS

(75) Inventors: Michael J Christie, Nashville, TN (US); David K. DeBoer, Franklin, TN (US); Michael C. Jones, North Webster, IN (US); Steven Wayne Smith, Fort Wayne, IN (US); Brad Alan Parker, Warsaw, IN (US); Charles W. Jaggers, Warsaw, IN (US); Derek A. Shrack, Leesburg, IN (US); James Ray Rogers, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 1244 days.

(21) Appl. No.: 10/748,443

(22) Filed: Dec. 30, 2003

(65) Prior Publication Data

US 2005/0154331 A1 Jul. 14, 2005

(51) Int. Cl.
*A61B 17/00* (2006.01)
(52) U.S. Cl. .............................. 606/79; 606/80; 606/82
(58) Field of Classification Search .................. 606/53, 606/54, 57, 79–96, 98, 99, 105
See application file for complete search history.

(56) References Cited

U.S. PATENT DOCUMENTS

| 4,004,581 A | 1/1977 | Heimke et al. |
| 4,116,200 A | 9/1978 | Braun et al. |
| 4,658,808 A | 4/1987 | Link |
| 4,738,256 A * | 4/1988 | Freeman et al. ............... 606/87 |
| 4,777,942 A | 10/1988 | Frey et al. |
| 5,047,033 A | 9/1991 | Fallin |
| 5,171,244 A | 12/1992 | Caspari et al. |
| 5,192,283 A | 3/1993 | Ling et al. |
| 5,207,680 A | 5/1993 | Dietz |
| 5,228,459 A | 7/1993 | Caspari et al. |
| 5,263,498 A | 11/1993 | Caspari et al. |
| 5,304,181 A | 4/1994 | Caspari et al. |
| D346,979 S | 5/1994 | Stalcup et al. |

(Continued)

FOREIGN PATENT DOCUMENTS

EP 0 595 956 7/1992

(Continued)

*Primary Examiner*—Eduardo C Robert
*Assistant Examiner*—Christina Negrelli
(74) *Attorney, Agent, or Firm*—Maginot, Moore & Beck (57) ABSTRACT

A milling system for creating a cavity in a bone includes a drive shaft, a frame for carrying a cutter and a cutter for cutting the cavity. The drive shaft has a proximal end and a distal end forming a portion of a drive joint for coupling the drive shaft to a cutter. The frame includes a frame shaft and a cutter mount, mounting a cutter at a first angle. The mount includes a bearing bracket extending laterally from the frame shaft to a bearing receiving a portion of a cutter and maintains the received cutter oriented at the first angle during rotation. The cutter has a head forming a portion of drive joint for coupling the cutter to a drive shaft. The cutter is received in the mount at the first angle and the drive shaft forms a second angle with the longitudinal axis less than the first angle.

21 Claims, 9 Drawing Sheets

U.S. PATENT DOCUMENTS

| | | | |
|---|---|---|---|
| 5,342,363 A * | 8/1994 | Richelsoph | 606/79 |
| 5,344,423 A | 9/1994 | Dietz et al. | |
| 5,395,376 A | 3/1995 | Caspari et al. | |
| D357,315 S | 4/1995 | Dietz | |
| 5,403,320 A | 4/1995 | Luman et al. | |
| 5,468,243 A * | 11/1995 | Halpern | 606/80 |
| 5,470,336 A | 11/1995 | Ling et al. | |
| 5,474,559 A | 12/1995 | Bertin et al. | |
| 5,486,180 A | 1/1996 | Dietz et al. | |
| 5,496,324 A | 3/1996 | Barnes | |
| 5,507,815 A | 4/1996 | Wagner et al. | |
| 5,507,833 A | 4/1996 | Bohn | |
| 5,534,005 A | 7/1996 | Tokish, Jr. et al. | |
| 5,540,694 A * | 7/1996 | DeCarlo et al. | 606/80 |
| 5,569,255 A | 10/1996 | Burke | |
| 5,593,411 A | 1/1997 | Stalcup et al. | |
| 5,601,563 A | 2/1997 | Burke et al. | |
| 5,607,269 A | 3/1997 | Dowd et al. | |
| 5,643,271 A * | 7/1997 | Sederholm et al. | 606/80 |
| 5,653,714 A | 8/1997 | Dietz et al. | |
| 5,683,395 A | 11/1997 | Mikhail | |
| 5,743,915 A | 4/1998 | Bertin et al. | |
| 5,755,803 A | 5/1998 | Haines et al. | |
| 5,769,855 A | 6/1998 | Bertin et al. | |
| 5,810,827 A | 9/1998 | Haines et al. | |
| 5,810,830 A | 9/1998 | Noble et al. | |
| 5,853,415 A | 12/1998 | Bertin et al. | |
| 5,860,981 A | 1/1999 | Bertin et al. | |
| 5,879,354 A | 3/1999 | Haines et al. | |
| 5,908,423 A * | 6/1999 | Kashuba et al. | 606/80 |
| 5,919,195 A * | 7/1999 | Wilson et al. | 606/80 |
| 5,957,925 A * | 9/1999 | Cook et al. | 606/87 |
| 5,968,049 A | 10/1999 | Da Rold | |
| 5,976,145 A | 11/1999 | Kennefick, III | |
| 5,993,455 A | 11/1999 | Noble | |
| 6,056,754 A | 5/2000 | Haines et al. | |
| 6,120,507 A | 9/2000 | Allard et al. | |
| 6,159,214 A | 12/2000 | Michelson | |
| 6,197,064 B1 | 3/2001 | Haines et al. | |
| 6,197,065 B1 | 3/2001 | Martin et al. | |
| 6,270,502 B1 | 8/2001 | Stulberg | |
| 6,287,342 B1 | 9/2001 | Copf et al. | |
| 6,318,651 B1 | 11/2001 | Spiering | |
| 6,432,141 B1 | 8/2002 | Stocks et al. | |
| 6,440,139 B2 | 8/2002 | Michelson | |
| 6,508,841 B2 | 1/2003 | Martin et al. | |
| RE38,058 E | 4/2003 | Fallin | |
| 6,589,285 B2 | 7/2003 | Penenberg | |
| 6,663,616 B1 | 12/2003 | Roth et al. | |
| 6,676,706 B1 | 1/2004 | Mears et al. | |
| 6,770,100 B2 | 8/2004 | Draenert | |
| 6,846,314 B2 * | 1/2005 | Shapira | 606/80 |
| 6,949,101 B2 * | 9/2005 | McCleary et al. | 606/80 |
| 2003/0130740 A1 | 7/2003 | Stocks et al. | |
| 2003/0171756 A1 | 9/2003 | Fallin et al. | |
| 2003/0187449 A1 | 10/2003 | McCleary et al. | |
| 2003/0220698 A1 | 11/2003 | Mears et al. | |
| 2004/0092951 A1 | 5/2004 | Serra et al. | |

FOREIGN PATENT DOCUMENTS

| | | |
|---|---|---|
| EP | 0 661 023 | 12/1994 |
| EP | 1 084 680 | 12/1994 |
| EP | 0 726 063 | 2/1996 |
| EP | 0 842 639 | 11/1997 |
| EP | 0 511 244 | 10/1998 |
| EP | 1 348 384 | 3/2003 |
| EP | 1 369 089 | 12/2003 |
| WO | WO 91/10408 | 7/1991 |
| WO | WO 92/10138 | 6/1992 |
| WO | WO 94/12123 | 6/1994 |
| WO | WO 03/082159 | 10/2003 |
| WO | WO 03/094698 | 11/2003 |
| WO | WO 02/102254 | 12/2003 |

* cited by examiner

MINIMALLY INVASIVE BONE MILLER APPARATUS

BACKGROUND AND SUMMARY

This invention relates to the field of artificial joint prostheses and, in particular, to an improved instrument for machining a precise cavity in bone for receiving a prosthesis.

For implantation of prosthetic stems, such as hip stems, accurate preparation of the bone or intramedullary canal is extremely important in order to guarantee good contact between the prosthesis stem and the bone. The underlying concept behind precise preparation is that a precise bone envelope reduces the gaps between the implant (i.e. prosthesis or prosthetic component) and the bone, thereby improving the initial and long-term bone ingrowth/fixation. The bone canal is presently prepared for implantation of a prosthetic stem by drilling and reaming a resected end of a bone, such as a femur, and then preparing an area adjacent the drilled hole to provide a seat for the prosthetic stem or a proximal sleeve coupled to the stem of a modular prosthetic system.

Modular prosthetic systems using proximal sleeves, stems, necks and heads, such as the S-ROM Modular Hip System, available from DePuy Orthopaedics, Warsaw, Ind., put much control in the hands of the surgeon, providing solutions for a variety of surgical scenarios, from primary total hip arthroplasty (THA) to the complex revision or DDH challenges. Such system provides such versatility because the provided plurality of stems, sleeves, necks and heads which can be assembled in a large number of configurations.

Preparation of the area adjacent the drilled hole may be accomplished by broaching or by milling. Broaches or rasps, when used for bone preparation, have limitations. One such limitation is the risk of fracture during broaching. Since broaching is done by pounding the broach into the bone, the bone tends to fracture. Additionally, both broaches and rasps suffer from a tendency to be deflected by harder sections of bone so that they do not create as precise a triangular cavity as can be created by a miller system. In a study that compared an intimate fill with robotically machined femora, Paul et al., found that broaching tore the trabecular bone, whereas femoral canal preparation with reamers was consistently more accurate. Paul, H. A., et al. "Development of s Surgical Robot for Cementless Total Hip Arthroplasty." *Clinical Orthopedics and Related Research* 285 December 1992: 57-66.

Thus, milling is currently the preferred method of bone preparation in many orthopaedic applications because it is an extremely precise method of bone preparation. A limitation of milling systems today is that they are typically formed so that the drive shaft extends at an angle relative to the remainder of the frame from the end of the miller cutter machining the bone. A fairly large incision must be made to accommodate such milling assemblies. A typical incision for preparing a femur for a total prosthetic hip replacement using a standard triangle miller system is nine inches long. It is not uncommon for incisions as large as 12 inches to be used in a total hip replacement procedure.

A standard triangle miller system typically includes a miller shell, a miller frame and a miller cutter having an end formed for coupling to a drill. A typical miller frame and miller cutter can be seen in U.S. Pat. No. 5,540,694 issued to DeCarlo, Jr. et al. on Jul. 30, 1996. This miller frame allows for precise machining of the triangular canal by a miller cutter held at an angle with respect to the shaft of the frame. The triangular canal facilitates an accurate fit of a proximal sleeve that distributes the load experienced by the prosthesis evenly and provides rotational stability. However, to accommodate this miller, it is necessary to make a fairly large incision which may be undesirable for cosmetic or other reasons.

The large incision is required because the miller cutter includes a fixed unprotected input shaft for connecting to and/or receiving motive (i.e. rotary) power from a drill or similar instrument. As such, the prior reamer is able to accept rotary input power with respect to only one direction. Typically, this direction is at 0° (i.e. "straight on") with respect to the reamer which is approximately thirty two degrees with respect to the shaft of the miller frame. Therefore, not only is the input power direction restricted, but this, in turn, restricts the angle at which the reamer may be used on a patient. Since the input shaft and the drill coupled thereto extend laterally beyond the edge of the miller frame an incision substantially larger than the width of the frame must be made to accommodate the reamer, frame and drill during surgery. Since the input shaft is unprotected the incision must be large enough to accommodate the reamer, fame, input shaft and drill without the input shaft engaging soft tissue.

In view of the above, it would be desirable to have a bone miller or guided reamer that could fit into a smaller incision during a surgical process.

It would be even further desirable to have a bone milling device as desired above that also is able to accept input rotary power from various angular orientations and/or allows bone milling device to be positioned at various angular orientations relative to the input rotary power.

A milling system is disclosed for creating a cavity in a bone. The cavity has a cross section which has a generally triangular profile having a first side generally parallel with an axis of the bone and a second side forming an acute angle with the first side. The cavity is contiguous with a pre-existing conical cavity in the bone. The system comprises a drive shaft, a frame for carrying a cutter and a cutter for cutting the cavity. The drive shaft has an axis, a proximal end configured for coupling to a drive means and a distal end configured to form a portion of a drive joint for coupling the drive shaft to a cutter. The frame includes a shaft having a longitudinal axis and a cutter mount for mounting a cutter at a first angle approximating the acute angle with respect to the shaft. The mount includes a bracket extending laterally from the shaft to a bearing configured to receive a portion of a cutter and maintain the received cutter oriented at the first angle during rotation. The cutter has a head configured to form a portion of a drive joint for coupling the cutter to a drive shaft. The drive shaft is coupled to the cutter to form the drive joint. The cutter is received in the mount at the first angle and the axis of the drive shaft forms a second angle with the longitudinal axis less than the first angle.

An apparatus for creating a cavity in a bone for receiving a prosthesis which has a conical portion and a projection of a generally triangular profile is disclosed. The apparatus comprises a shell, a frame, and a cutter. The shell includes a conical portion which defines a longitudinal axis and a shaft-receiving cavity for receiving a frame. The frame includes a shaft, a drive shaft and a shield. The shaft is received by the shaft-receiving cavity and is movable with respect to the shell along the longitudinal axis. The frame is configured to carry the cutter disposed at an acute angle relative to the longitudinal axis. The drive shaft is disposed at an angle relative to the longitudinal axis less than the acute angle and is configured at one end to couple to and drive the cutter. The shield is disposed about portions of the drive shaft adjacent the one end. The cutter has a generally triangular profile and is carried by the frame and is configured to mate with and be driven by the drive shaft.

A method for cutting a triangular cavity in bone includes the steps of providing a cutter having a cutter bearing, providing a frame, journaling the cutter bearing in the frame incising the patient, providing a drive shaft and cutting the cavity. The provided cutter comprises a cutting surface having an outer diameter and a cutter bearing at one end of the cutting surface having an outer diameter larger than the outer diameter of the cutting surface. The provided frame has a shaft movable relative to the bone to be prepared which comprises a frame bearing which is complementary to the cutter bearing and which has an inner diameter which is larger than the outer diameter of the cutter's cutting surface and is configured to hold the bearing at a first acute angle relative to the shaft. The shaft has a width extending between the shaft and the bearing.

Journaling the cutter bearing in the frame is accomplished by passing the cutter's cutting surface through the frame bearing and engaging the cutter bearing with the frame bearing. The incising occurs adjacent the bone to be prepared to form an incision having a length approximating the width of the provided frame. The provided drive shaft includes portions configured to couple to and drive the cutter when the drive shaft is disposed at a second angle relative to the shaft which second angle is less than the first angle. The cavity is cut by driving the cutter with the drive shaft disposed at the second angle and moving the frame relative to the bone.

The disclosed triangular miller is configured to reduce the size of incision required for preparation of a bone with a reamer or milling tool to receive a prosthetic stem therein. The disclosed triangular miller frame includes one or more of the following features, either alone or in combination. A drive shaft alignment bracket supporting a drive shaft. A constant velocity joint at the interface between the drive shaft and the milling tool or reamer facilitating various drive shaft angles. A spring loaded sleeve surrounding portions of the drive shaft to protect soft tissue adjacent to the bone being prepared.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

BRIEF DESCRIPTION OF THE DRAWINGS

FIG. 14 is a side elevation view of the miller cutter of FIG. 1;

FIG. 15 is a sectional view taken along line 15-15 of the miller cutter of FIG. 14 showing a reamer body having a bearing head attached thereto formed to include a drive tip-receiving cavity for receipt of the tip of the drive shaft and having a dowel extending across the cavity for receipt in a slot in the end of the tip of the drive shaft; and, FIG. 16 is an end view taken along line 16-16 of the miller cutter of FIG. 14 showing the dowel extending across the drive tip-receiving cavity.

Corresponding reference characters indicate corresponding parts throughout the several views. Like reference characters tend to indicate like parts throughout the several views.

DETAILED DESCRIPTION OF THE INVENTION

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The disclosed triangle miller assembly 20 allows a surgeon to machine (mill) bone through a smaller incision 18 compared to existing surgical instruments. The disclosed miller assembly 20 is derived from a standard miller assembly such as that disclosed in DeCarlo, Jr. et al., Instrument for Cutting Bone, U.S. Pat. No. 5,540,694, issued Jul. 30, 1996, the disclosure of which is hereby incorporated herein by this reference. A miller frame similar to that disclosed in DeCarlo, Jr. et al. may be modified by adding a strike plate 50 at the proximal end of the frame 24, a shielded drive shaft assembly 120 and a drive shaft alignment bracket 100 and by moving the reamer bracket downwardly and inwardly. The reamer bracket 52 is moved in a manner that maintains the alignment of the bushing axis 55 with the axis 99 of the tip-receiving hole 58. Generally, however, the disclosed miller frame 24 and miller cutter 22 of miller system 20 are fabricated independently from any prior art system.

The drive shaft bracket 100 is configured to support the shielded drive shaft assembly 120 substantially parallel to the frame axis 66. The strike plate 50 facilitates exerting down pressure needed during the milling process. A mallet maybe used to strike the strike plate 50 if required. The strike plate 50 also facilitates extraction of the miller frame 24 following bone cutting.

Additionally, the miller cutter 22 used with the disclosed milling system 20 differs from that disclosed in DeCarlo, Jr. et al. Miller cutter 22 is shorter and is configured to be coupled through a universal coupling with a drive shaft 128 having an axis 142 not coincident with the axis 113 of the miller cutter 22.

The movement of the bearing bracket 64 downwardly and inwardly reduces the effective width 32 (from the shaft 48 to the edge of the bracket 64) of the miller frame 24. However, this reduction in the effective width 24 of the frame contributes only a small amount to the reduction in the size of the incision 18 required to perform a prosthetic surgery. The majority of the reduction in the size of the surgical incision 18 arises from modification of the miller cutter 22 to permit coupling to a drive shaft 128 that is not parallel to the axis of the miller cutter 22. Due to this modification the cutter 22 and drive shaft 128 need not extend beyond the effective width 32 of the miller frame 24. By providing a protective sleeve 124 surrounding the drive shaft 128, soft tissue cannot engage the spinning shaft 128 during operation and clearance beyond the drive shaft 128 can be further reduced.

The drive shaft alignment bracket 100 supports the drive shaft 128 in a position parallel to the axis 66 of the shaft 48 of the miller frame 24 so that the entire assembly presents a uniform cross section from the top of the reamer upward. When the drive shaft assembly is parallel to the axis 66 of the shaft 48, the miller frame 24 has a maximum width approximately equal to the effective width 32. The drive shaft 128 is coupled to the miller cutter 22 through a universal coupling. The sleeve 124 protects the soft tissue surrounding the bone being cut from the drive shaft 128. Thus, the surgical incision 18 required to use the disclosed miller system 20 is only slightly larger than the effective width 32 of the miller frame 24. The disclosed miller frame 24 has an effective width 32 of approximately 2.25 inches compared to the effective width of approximately 2.5-2.75 inches of the miller frame of a typical miller system for a hip prosthesis.

Figure 2:
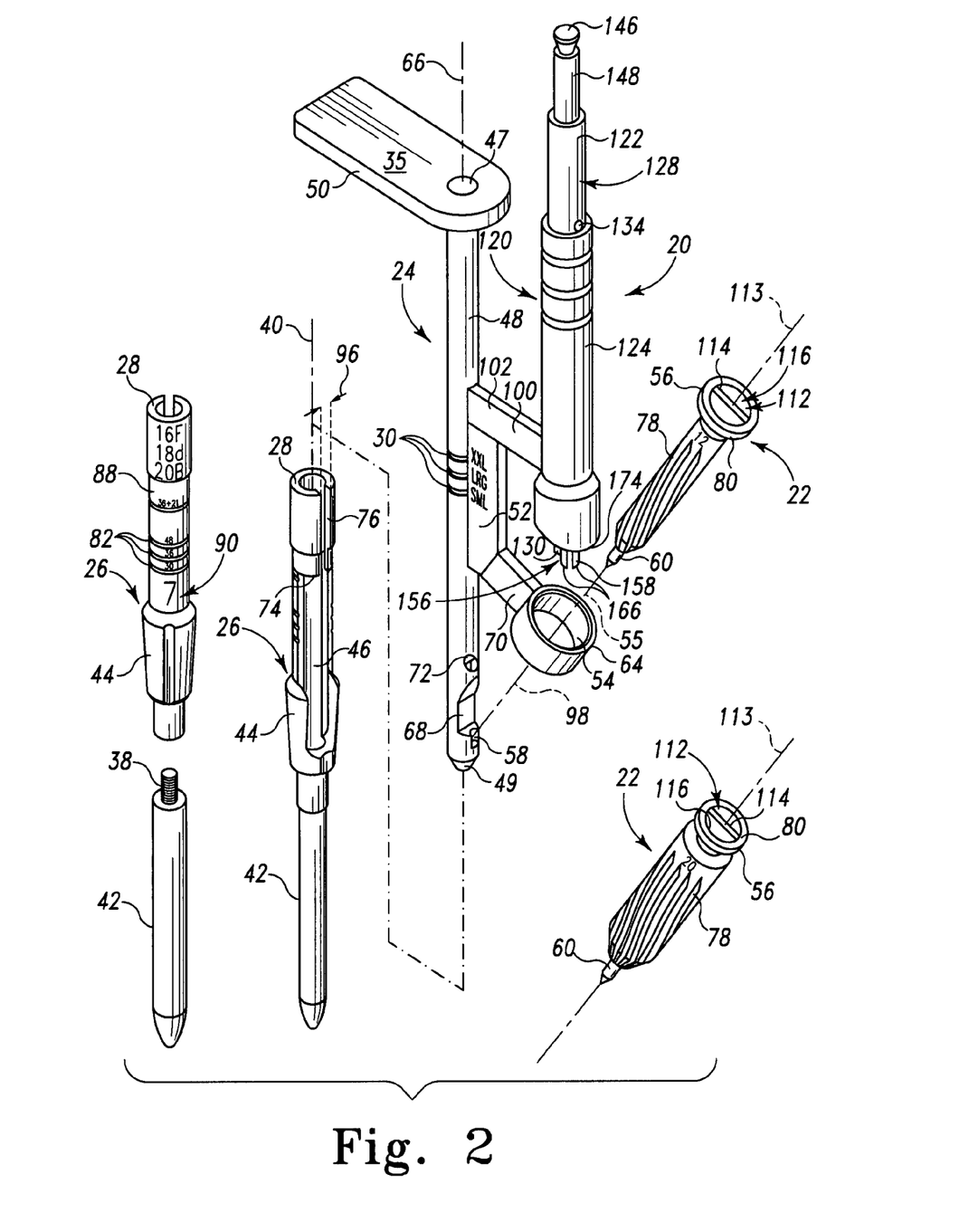
FIG. 2 is an exploded view of the miller system of FIG. 1 showing the miller frame with the shielded drive shaft assembly in a retracted and locked configuration, two miller cutters intended to represent a plurality of miller cutters each configured to be held by miller frame, two miller shells intended to represent a plurality of miller shells each configured to slidably receive the miller frame and two pilot shafts each configured to mount to each miller shell.
Figure 3:
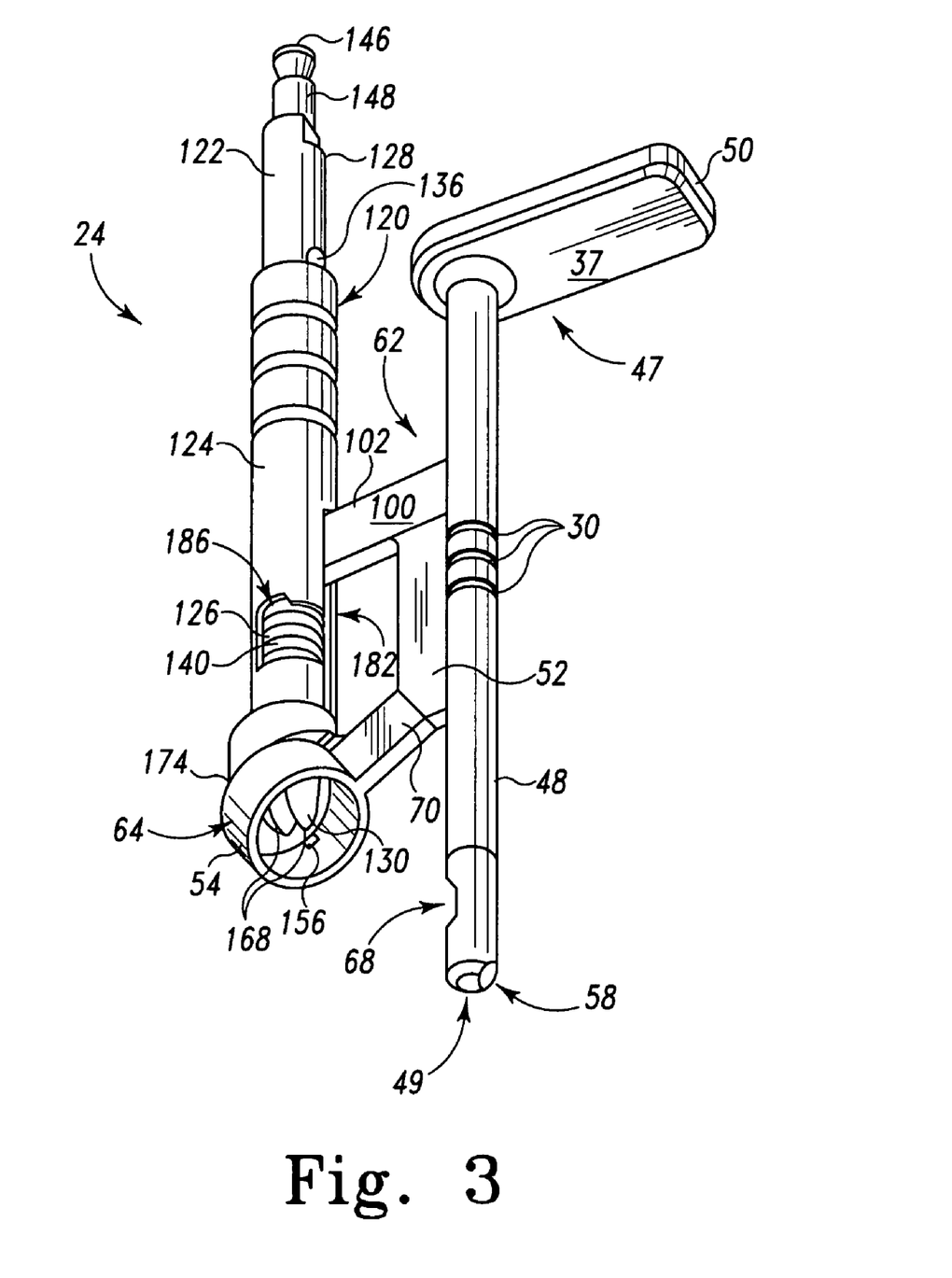
FIG. 3 is a perspective view of the miller frame of FIG. 1 showing the wire assembly and shielded drive shaft assembly.
Figure 4:
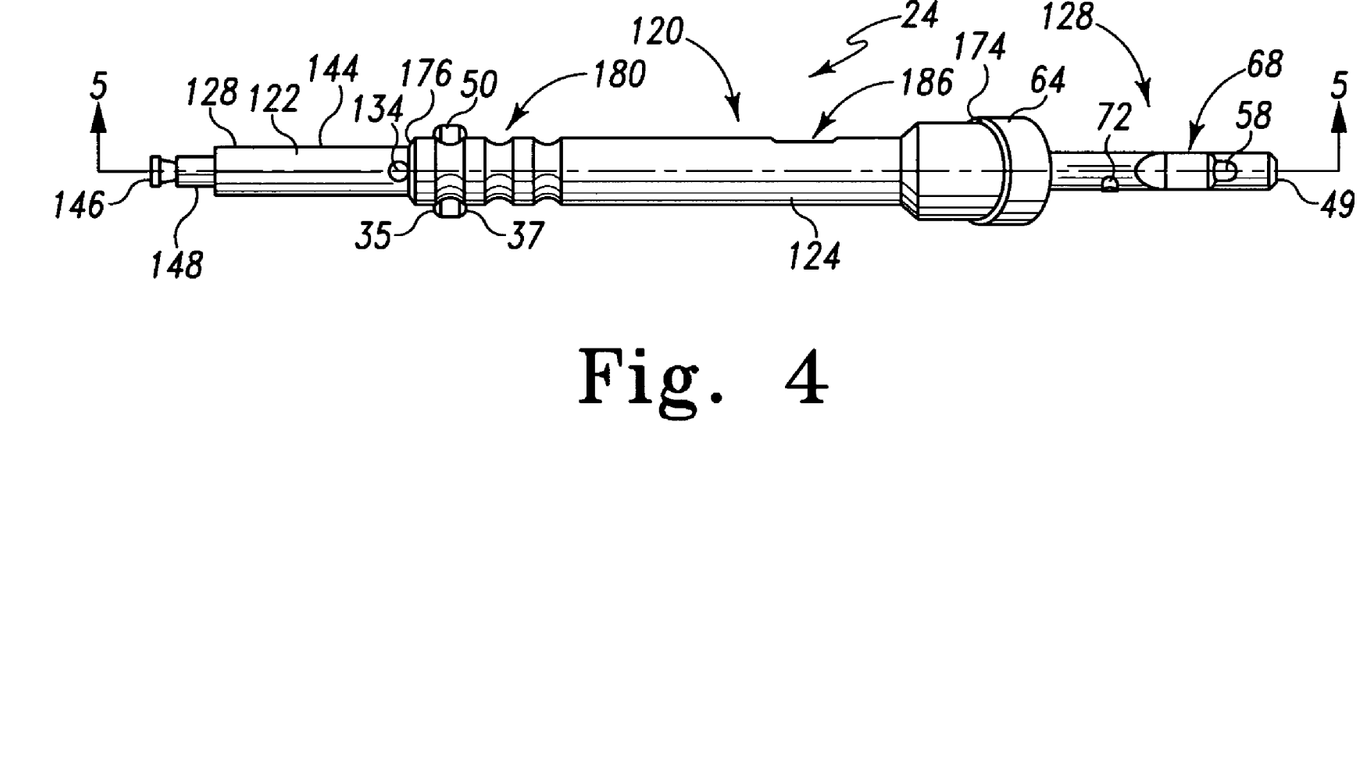
FIG. 4 is a front view of the miller frame of FIG. 3.

With reference now to the drawings, wherein like reference characters designate like or corresponding parts throughout the several views, there is shown in FIG. 2 an exploded view of surgical instrument or triangle miller system 20 constructed in accordance with the invention. Instrument 20 includes miller cutter 22 for cutting the desired triangular-shaped cavity, miller frame 24 for carrying the miller cutter 22, miller shell 26 for registering the instrument with a pre-existing conical cavity in the patient's bone, a pilot shaft 42 removably attached to the miller shell 26 for insertion in a prepared medullary canal of the patient's bone and indicators 28, 30 for indicating the longitudinal location of miller frame 24 relative to miller shell 26.

While in the illustrated embodiment, only two miller shells 26, two pilot shafts 42, and two miller cutters 22 are shown, it is to be understood that a plurality of miller shells, pilot shafts and miller cutters may be made available to the surgeon using the disclosed miller instrument 20. Each miller cutter 22 is configured to be held by miller frame 24. Each miller shell 26 is configured to slidably receive the miller frame 24. Each pilot shaft 42 is configured to mount to each miller shell 26. Thus a plurality of miller instruments 20 may be formed each utilizing the same miller frame 24.

Miller shell 26 has a longitudinal axis 40. Pilot shaft 42 is removably attached to the main body of the miller shell 26 by, for example, a screw thread 38. The miller shell 26 also has an external conical surface 44 which engages the wall of the pre-existing conical cavity, as shown, for example, in FIG. 1. In addition, the miller shell 26 has shaft-receiving cavity 46 for receiving the shaft 48 of the miller frame 24 and allowing the longitudinal axis 66 of the shaft 48 of the miller frame 24 to move along longitudinal axis 40.

In the illustrated embodiment, miller frame 24 includes a wire assembly 62 and a shielded drive shaft assembly 120. The wire assembly 62 includes a shaft 48, a strike plate 50, and a guide tab bracket 52, a cutter bearing bracket 64 and a drive shaft alignment bracket 100. Shaft 48 includes a proximal end 47, a distal end 49 and a longitudinal axis 66. The strike plate 50 is coupled to the proximal end 47 of shaft as shown, for example, in FIGS. 1-7 and 10. Extending radially outwardly from shaft 48 is guide tab bracket 52, cutter bearing bracket 64 and drive shaft alignment bracket 100. Cutter bearing bracket 64 includes a mounting arm 70 and a bearing 54. Bearing 54 engages complementary cutter bearing 56 on cutter 22. The drive shaft bracket 100 includes a mounting arm 102 and a receiver 104 that receives shielded drive shaft assembly 120.

The strike plate 50 is a rounded rectangular plate including a top surface 35 substantially parallel to a bottom surface 37. Strike plate 50 is formed to include a mounting hole (obscured by proximal end 47 of shaft 48 in FIG. 5) adjacent one end through which the proximal end 47 of shaft 48 is received. In the illustrated embodiment, shaft 48 is welded to strike plate 50 so that strike plate 50 extends laterally from the axis 66 of the shaft 48 in the opposite direction from bracket 52. The top planar surface 35 of the strike plate 50 facilitates exerting downward pressure during the milling process. The strike plate 50 can also be used to remove the miller frame 24. Either planar surface 35, 7 may be struck with a mallet to facilitate advancing the miller system 20 into the bone when the top surface 35 is struck or removal of the miller system 20 from the bone cavity when the bottom surface 37 is struck.

Shaft 48 also includes tip hole 58 which engages complementary tip 60 on cutter 22. Shaft 48 includes pin 72 which engages surface 74 of miller shell 26 during withdrawal of the miller shell 26 from the patient's bone (see below). Additionally, shaft 48 is formed to include a flute cavity 68 configured to allow the flutes of a cutter 22 to turn therein when the tip 60 is received in tip hole 58.

Shaft 48 is sized to fit within shaft-receiving cavity 46 of miller shell 26 with bracket 52 and mounting arms 70, 102 being slidable in slot 76 formed in the upper portion of the miller shell 26. Pin 72 is also sized to fit through slot 76. To that end, guide tab bracket 52, mounting arms 70, 102 of cutter brackets 64 and drive shaft alignment bracket 100, respectively, have a thickness 94 slightly less than the width of the slot 76. Illustratively, thickness 94 of bracket 52 and mounting arms 70, 102 is 0.186 inches while the width 96 of slot 76 is 0.1975 inches. Bracket 52 and mounting arms 70, 102 are located at different angular positions around the circumference of shaft 48 from pin 72 so that the shaft 48 must be rotated about its longitudinal axis 66 to first align pin 72 with slot 76 and then sequentially align bracket 52 and mounting arms 70, 102 with slot 76 during assembly of the instrument 20.

Figure 1:
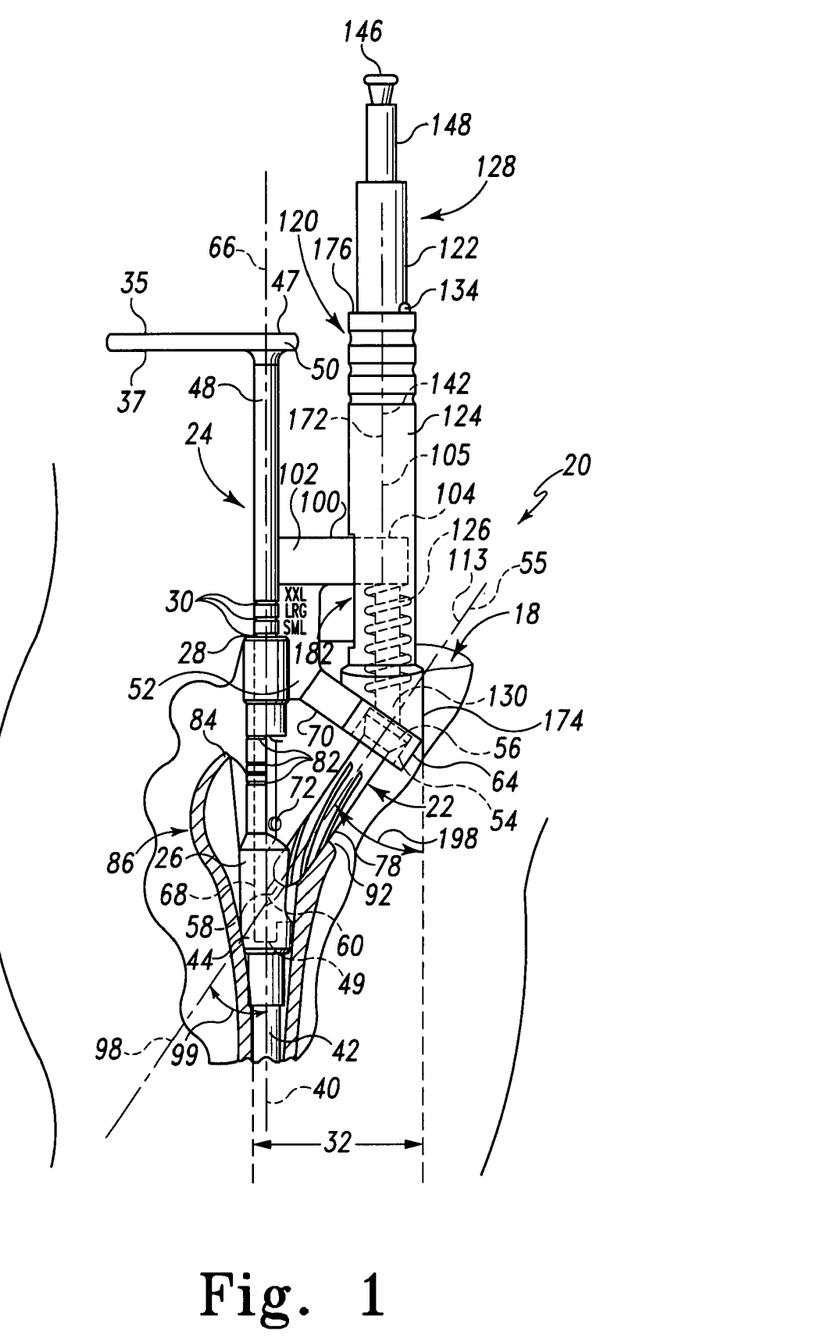
FIG. 1 is a view with parts broken away of a miller system inserted through an incision into a resected femur of a patient using a selected miller shell and pilot stem 20 and a selected miller cutter held in the miller frame received in the selected miller shell.

Referring now to FIG. 1 there is shown a triangular milling instrument 20 including a miller shell 26, a miller frame 24, a pilot shaft 42 and a cutter 22. The miller frame 24 is slidably received in the miller shell 26 for reciprocal movement along the longitudinal axis 40 of the miller shell 26. The pilot shaft 42 is received in a previously reamed cylindrical cavity. Pilot shaft 42 is coupled to miller shell 26 to align the axis 40 of miller shell 26 relative to the cylindrical cavity. The conical surface 44 of the miller shell 26 is received in the previously reamed conical cavity. The pilot shaft 42 and miller shell 26 are selected from the plurality of pilot shafts and miller shells based on the size of the reamers used to form the cylindrical and conical cavities, respectively.

The shaft 48 of the wire assembly 62 of the miller frame 24 includes a longitudinal axis 66 which, when the shaft 48 is received in the miller shell 26, as shown, for example, in FIG. 1, coincides with the longitudinal axis 40 of miller shell 26. The shaft 48 is formed to include indictors 30 thereon for alignment with indicator 28 on the miller shell 26 in a well known manner. Near its distal end 49, shaft 48 is formed to include an angled tip-receiving hole 58 extending through the longitudinal axis 66. The tip-receiving hole 58 is sized and configured to receive the tip 60 of a reamer or miller cutter 22 for rotation therein. Tip-receiving hole 58 is formed concentrically about an axis 98. Illustratively axis 98 forms an angle 99 with respect to the longitudinal axis 66 of the shaft 48. Angle 99 corresponds to the angle the projection forms with the body of the sleeve of the prosthesis and the angle of the triangular cavity to be formed in the bone. Illustratively, angle 99 is thirty one and one tenth degree (31.1°).

As shown, for example, in FIGS. 1-6, 10, the wire assembly 62 of triangle miller frame 24 is formed by welding the shaft 48 and the integrally formed guide tab bracket 52 to the mounting arm 70 of the reamer bushing bracket 64 and the mounting arm 102 of the drive shaft bracket 100. Reamer bushing bracket 64 is mounted to align the axis 55, about which bearing 54 is concentrically formed, with the axis 99 about which tip-receiving hole 58 is formed. The drive shaft alignment bracket 100 is mounted to align the longitudinal axis 105 of the receiver 104 to be parallel with the longitudinal axis 66 of the shaft 48 and to intersect with the axis 55 of the bearing 54, as shown, for example, in FIG. 10. Guide tab 52, and mounting flanges 102, 70 of drive shaft bracket 100 and reamer bushing bracket 64, respectively, are all aligned as shown, for example, in FIG. 6, so that they slide within the channel 76 formed in miller shell 26.

The shielded drive shaft assembly 120 includes a drive shaft mechanism 122, a protective sleeve 124 and a spring 126. Protective sleeve 124 is disposed around portions of the drive shaft mechanism 122 that might be inserted into a surgical incision 18. Spring 126 urges the drive shaft mechanism 122 and protective sleeve 124 distally to induce drive shaft mechanism 122 to couple with miller cutter 22. As shown, for example, in FIG. 5, the drive shaft mechanism 122 includes a drive shaft 128, a drive nose 130, a retainer dowel 132, a release button 134, a set screw 136, and a bias spring 138.

Figure 7:
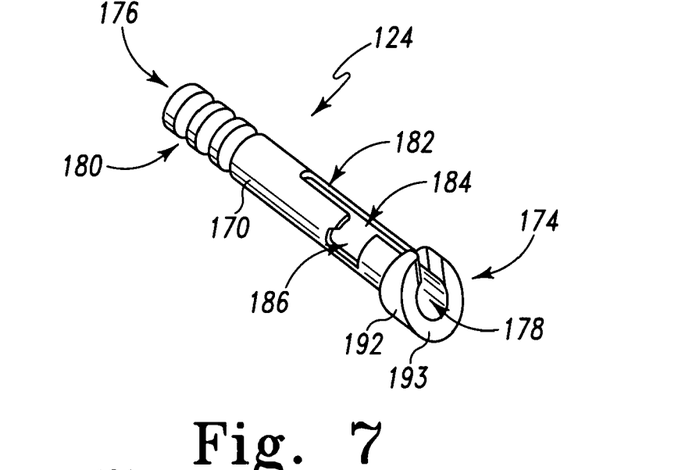
FIG. 7 is a perspective view of the protective sleeve of the shielded drive shaft assembly of the miller frame of FIG. 4.
Figure 8:
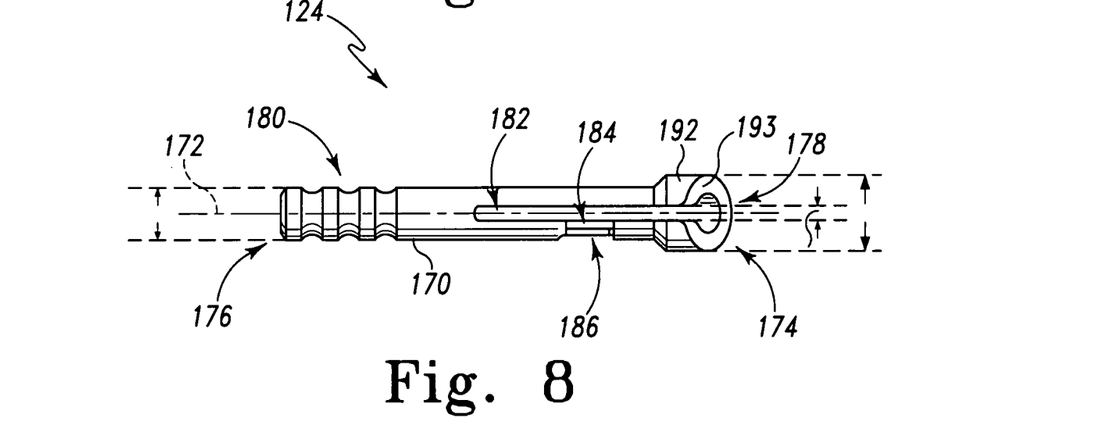
FIG. 8 is a back plan view of the protective sleeve of FIG. 7.
Figure 9:
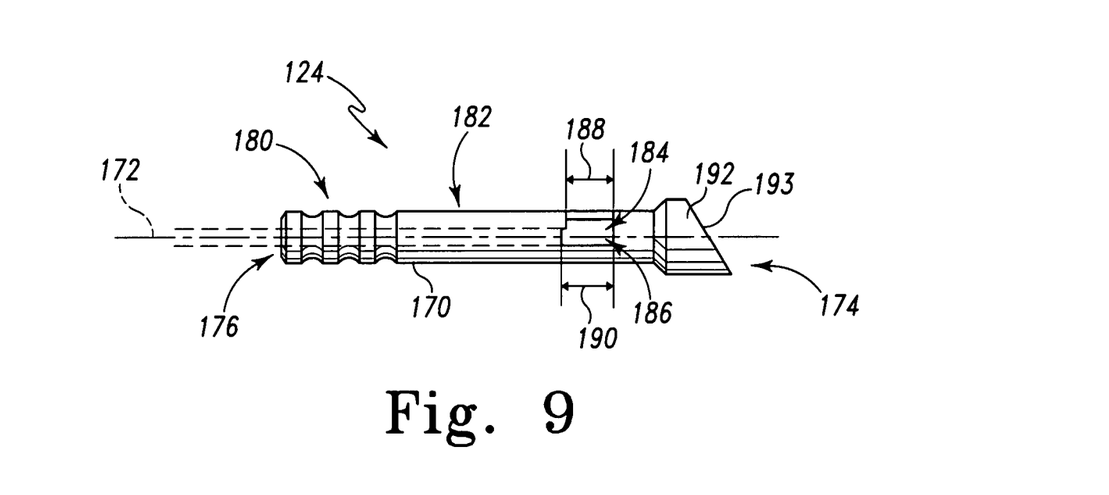
FIG. 9 is a side elevation view of the protective sleeve of FIG. 8.
Figure 10:
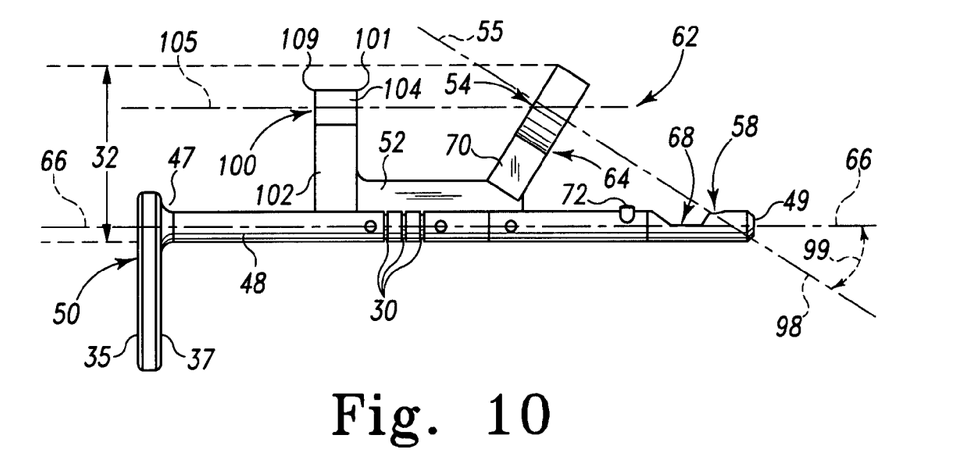
FIG. 10 is a plan view of the wire assembly of the miller frame showing a shaft, a strike plate, a guide tab bracket, a miller cutter bracket and a drive shaft alignment bracket.
Figure 11:
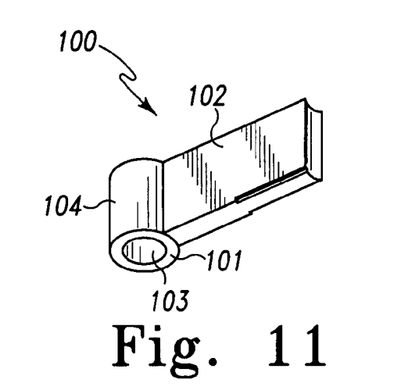
FIG. 11 is as perspective view of the drive shaft alignment bracket of the wire assembly of FIG. 10.
Figure 12:
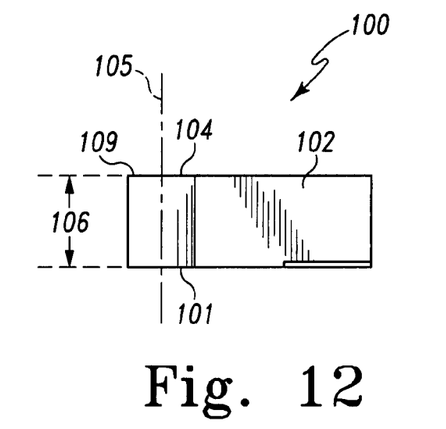
FIG. 12 is an elevation view of the drive shaft alignment bracket of FIG. 11.
Figure 13:
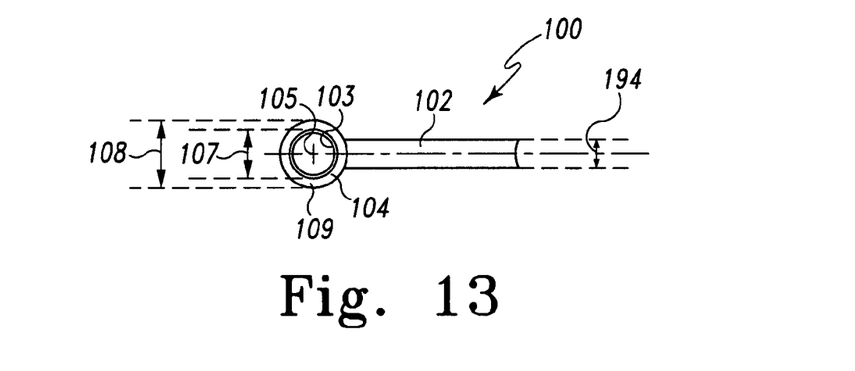
FIG. 13 is a plan view of the drive shaft alignment bracket of FIG. 11.

As shown generally in FIGS. 1-5 and more particularly in FIGS. 7-9, protective sleeve 124 includes a body 170 with a lumen 178 extending longitudinally therethrough. The body 170 and lumen 178 are formed generally concentrically about a longitudinal axis 172 extending between a distal end 174 and a proximal end 176 of the sleeve 124. The lumen 178 is sized to receive the central portion 144 and distal portion 142 of drive shaft 128, the receiver 104 of drive shaft bracket 100, the spring 126 and the drive nose 132 therein. Illustratively, lumen 178 has a diameter 180 (FIG. 5) slightly greater than the outside diameter 145 of central portion 144 of drive shaft 128, the outside diameter 108 of receiver 104, the outside diameter of the spring 126 and the outside diameter 160 of drive nose 130.

Adjacent the proximal end 176, the body 170 is formed to include a grip 180 to facilitate grasping the sleeve 124. The proximal end 176 of sleeve 124 engages release button 134 extending radially outwardly from a stepped cavity formed in the central portion 144 of drive shaft 128. Distal end 174 is formed to include a hood 192 sized to cover proximal surface 53 of bushing 54. A tapered wall extends between hood 192 and the remainder of body 170 of sleeve 124 to minimize the trauma to surrounding tissue coming in contact with the sleeve during removal of the miller cutter 22 from the incision 18.

The sleeve 124 includes a slit 182 that facilitates loading and unloading of the miller cutters 22 onto the miller frame 24. The slit 182 extends through the body 170 and communicates with the lumen 178. The slit 182 extends through the end wall 193 upwardly for a length greater than the minimum displacement between the proximal surface 109 of the drive shaft bracket 100 and the proximal wall of the bushing 54. The slit has a width 183 slightly greater than the thickness 94 of the mounting arm 102 to facilitate mounting arm 102 sliding therein. In the illustrated embodiment, slit 182 has a width 183 of 0.200 inches.

A miller cutter 22 is loaded onto the frame 24 by pulling the sleeve 124 back against the bias spring 126 until the opening 184 of the notch 186 on the sleeve 124 is lined up with the mounting arm 102 on the drive shaft bracket 100 of the miller frame 24. Once the sleeve 124 is lined up with the mounting arm 102, the sleeve 124 is twisted about its longitudinal axis 172 so that the mounting arm 102 passes through the opening 184 of, and is received in, the notch 186 in the sleeve 124.

In the illustrated embodiment, opening 184 has a width 188 slightly larger than the width 106 of the mounting arm 102 of the alignment bracket 100. Also, notch 186 has a width 190 greater than both the width 188 of the opening 184 and the width 106 of the mounting arm 102. Opening 184 and notch 186 are positioned along the slit so that, when the mounting arm 102 is received in the notch 186, miller cutters 22 may be loaded and unloaded without interference from the sleeve 124 or the drive shaft mechanism 122.

When the mounting arm 102 is received in the notch 186, the bracket 100 and sleeve 124 cooperate to overcome forces stored in the bias spring 126 and retain the sleeve 124 and the shaft mechanism 122 in a retracted position, as shown, for example, in FIG. 2. The sleeve 124 and drive shaft mechanism 122 are locked in this retracted position so that the miller cutters 22 can be loaded or unloaded.

The drive shaft 128 and sleeve 124 both move upward (compressing the spring 126 between the proximal end wall 162 of the ball nose drive 130 and the distal wall 101 of the receiver 104 of the drive bracket 100) during insertion and removal of the miller cutters 22. The arm 102 of the drive bracket 100 is received in the side opening notch 186 in the sleeve 124 when the sleeve 124 is twisted 90 degrees (or less) to lock the sleeve 124 and drive shaft 128 in a retracted position.

The protective sleeve 124 is removed from the miller frame 24 by depressing the release button 134 on the drive shaft 128 to compress a spring 138 held therein against the set screw 136. Once the release button 134 is depressed, the soft tissue protector sleeve 124 is free to slide upwardly and off of the drive shaft assembly 122.

Figure 5:
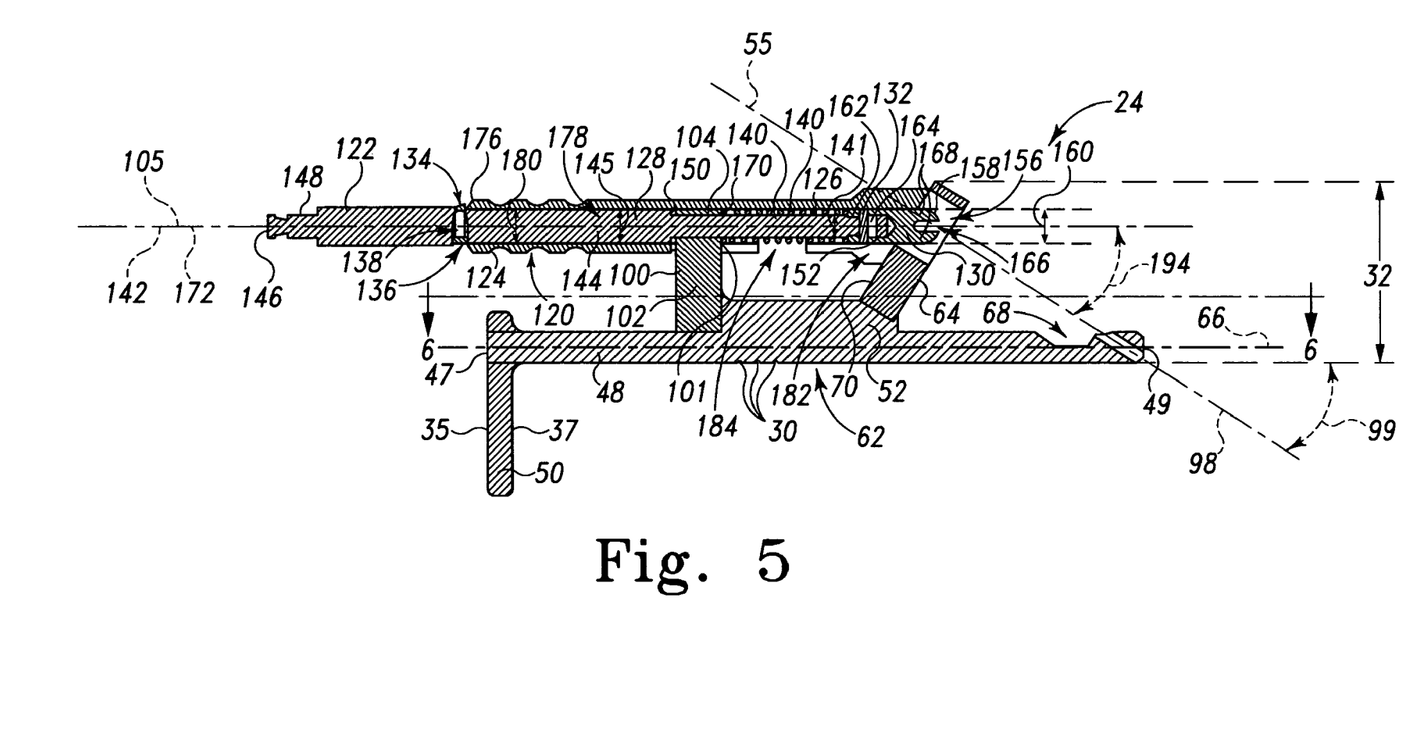
FIG. 5 is a sectional view taken along line 5-5 of the miller frame of FIG. 4.
Figure 6:
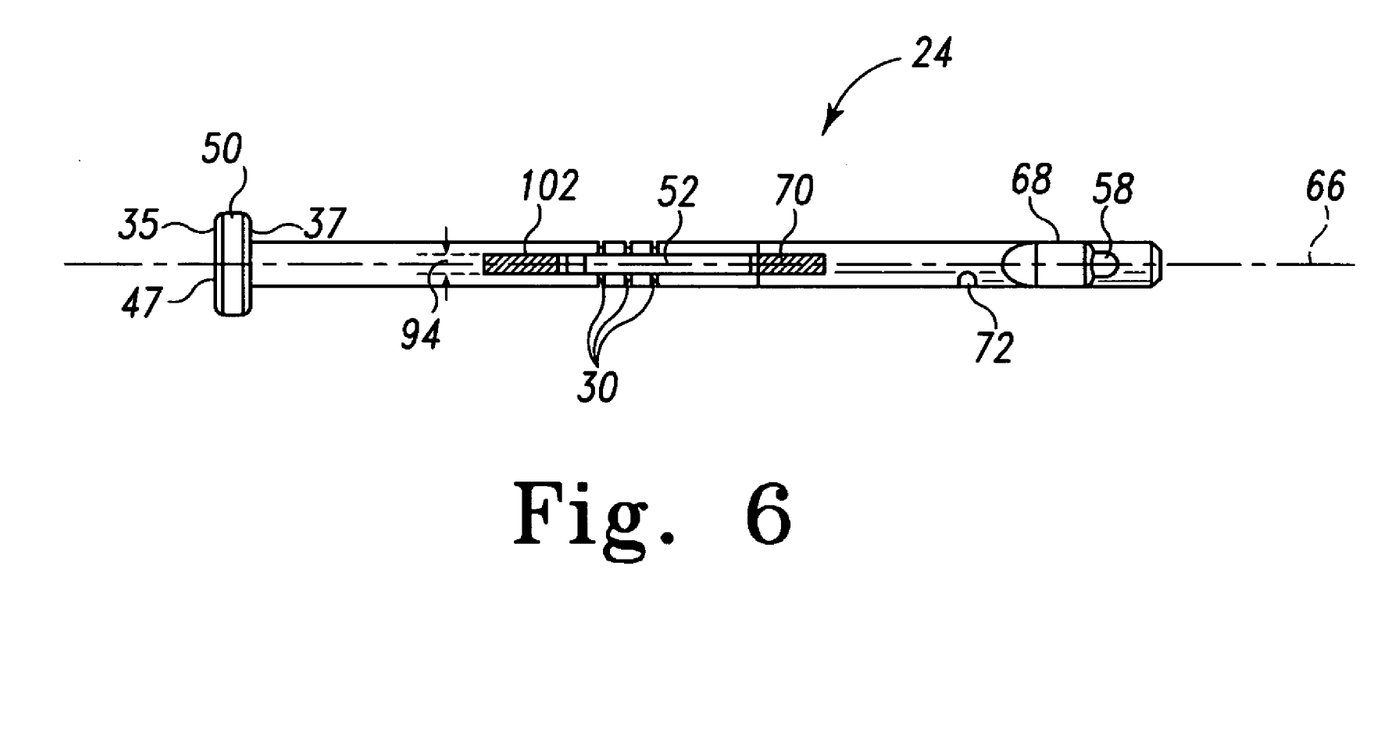
FIG. 6 is a sectional view taken along line 6-6 of the miller frame of FIG. 5.

As shown, for example, in FIG. 5, drive shaft 128 includes a proximal portion 148, a central portion 144 and a distal portion 140 all formed generally concentrically about axis 142. Central portion 144 has diameter 145 greater than the diameter of proximal portion 148 and the diameter 141 of distal portion 140. Proximal portion 148 is formed to facilitate coupling to rotary drive means such as a drill (not shown). The distal portion 140 of drive shaft 128 is received through an aperture defined by a cylindrical interior wall 103 formed concentrically about longitudinal axis 105 of the receiver 104 of drive shaft alignment bracket 100. Cylinder interior wall 103 has a diameter 107 slightly greater than the diameter 141 of distal portion 140 of shaft 128 to permit the shaft 128 to turn freely therein. Cylinder interior wall 103 has a diameter 107 less than the diameter 145 of central portion 144. Thus, proximal wall 109 of receiver 104 acts as a stop against which annular wall 150 extending between central portion 144 and distal portion 140 engages to limit distal movement of drive shaft assembly 122 when the sleeve 124 is removed.

In the illustrated drive shaft mechanism 124, the drive shaft 128 is connected at its distal end 152 to the drive nose 130. As shown, for example, in FIG. 5, drive nose 130 is formed to include a cavity 164 extending through its proximal end wall 162 into the body of drive nose 130. Cavity 164 is sized to receive the distal end 152 of drive shaft 128 therein. Proximal end of drive nose 132 is formed to include a dowel hole (obscured by dowel 132) extending laterally through the body and through the cavity 164. Distal end 152 of drive shaft 128 is likewise formed to include a dowel hole (obscured by dowel 132) extending laterally therethrough. When distal end 152 of drive shaft 128 is received in cavity 164, dowel holes are aligned and an appropriately sized retention dowel 132 is inserted therethrough to couple drive nose 130 to drive shaft 128. Dowel 132 is preferably welded in place to prevent the dowel 132 from falling out within a body cavity during use.

The distal end 156 of drive nose 130 is formed to serve as a slotted sphere component of a pinned-sleeve shaft coupling. Thus distal end 156 of drive nose 130 has a hemi-spherical end wall 158 through which a slot 166 is formed to create forks 168. Slot 166 has a width slightly greater than the diameter of a dowel pin 114 extending transversely across a cavity 116 formed in the head 80 of the cutter 22. The head 80, cavity 116 and dowel pin 114 of the cutter 22 and the fork 128 on the spherical distal end 156 of the drive nose 130 cooperate to form a pinned-sleeve shaft coupling. A pinned-sleeve shaft coupling is one type of a universal coupling or drive joint that facilitates driving cutter 22 with a drive shaft 128 of drive shaft assembly 122 that has a longitudinal axis 142 forming an angle 194 with the longitudinal axis 113 of the cutter 22. It is within the scope of the disclosure for drive shaft 128 to be coupled to cutter 22 using other universal couplings, such as, for example, a Hooke's joint, a pinned sphere shaft coupling, a grooved-sphere joint or the like or a constant velocity joint such as, for example, forked shafts with a slotted joint and a spigot joint extending therebetween, a triple strand spring, a Rzeppa, a Bendix-Weiss joint or the like.

Figures 14, 15, 16:
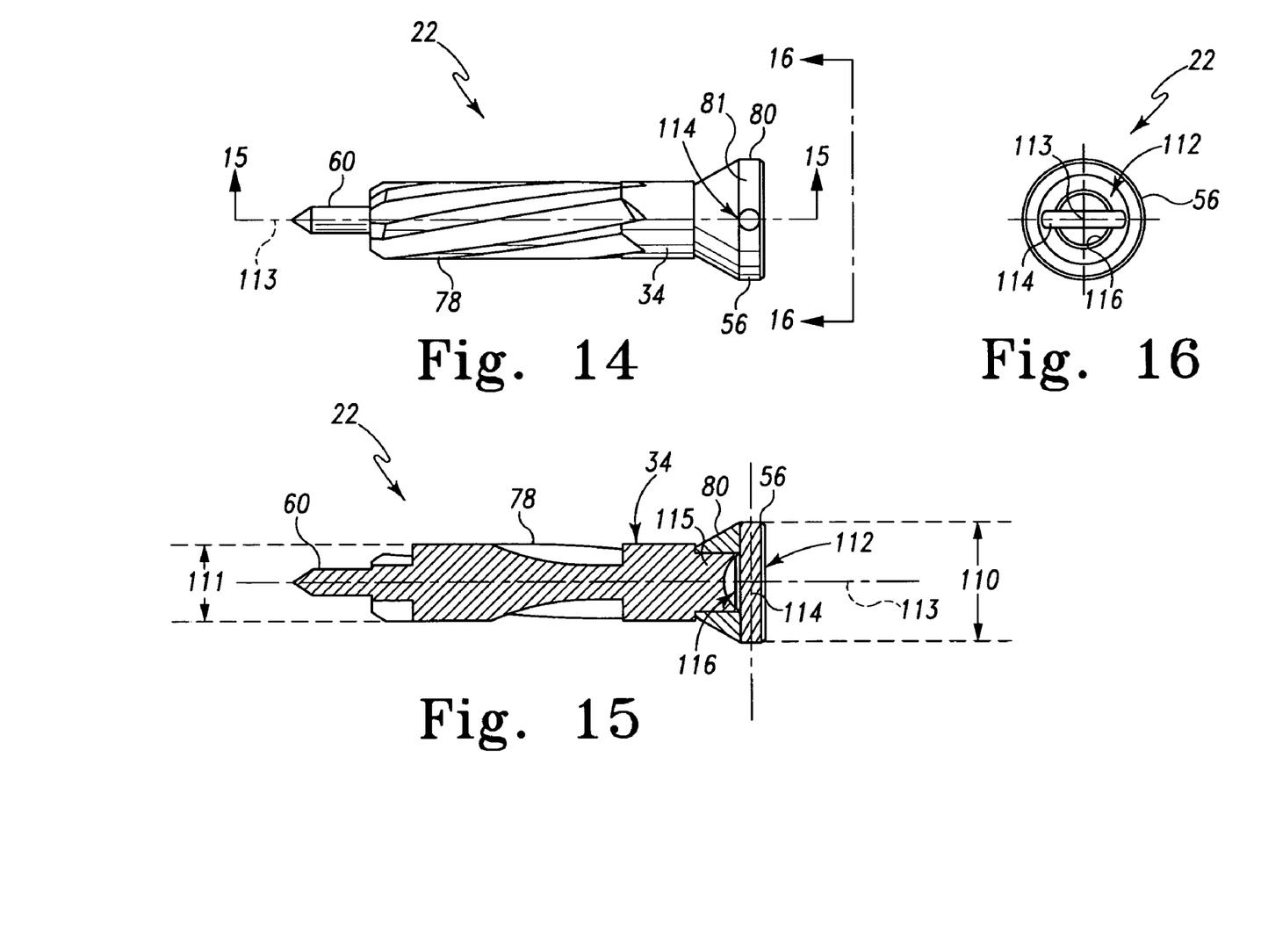

As shown, for example, in FIGS. 14-16, miller cutter 22 is a reamer formed about an axis 113 about which it spins. Miller cutter 22 includes a main body 34, a head 80 and a dowel pin 112. Main body 34 includes a tip 60, a cutting surface 78 and a stem 115. Tip 60 is formed concentrically about axis 113 and is sized to be received in tip-receiving cavity 58. Stem 113 is formed concentrically about longitudinal axis 113 and is sized to be received within head 80, as shown, for example, in FIG. 15. Head 80 and stem 113 are formed to include a cavity 116 having a hemi-spherical end wall for receipt of hemisherical end wall 158 of drive tip 130 therein. Head 80 has a cylindrical side wall 81 concentrically formed about axis 113. Cylindrical side wall 81 has a diameter 110 slightly less than the inside diameter of bushing 54 so that head 80 may be received in bushing. Head is formed to include two diametrically opposed mounting holes (obscured by dowel 114) through which dowel pin 114 is received. Dowel pin 114 is disposed extending across the cavity 116 to cooperate therewith to form the pin-sleeve of the pinned-sleeve shaft universal coupling.

Those skilled in the art will recognize that when miller cutter 22 is received in miller frame 24, tip 60 is received in tip-receiving hole 58 and head 80 is received in bushing 54. When cutter 22 is so received, the axis 113 of cutter 22 is coincident with axis 99 of tip-receiving aperture 58 and with axis 55 of bushing 54. Thus, axis 113 of cutter 22 forms an angle with longitudinal axis 66 of shaft 48 equal to angle 99 and forms an angle with longitudinal axis 142 of drive shaft 28 that is equal to angle 194.

During assembly of instrument 20, cutter 22 is inserted into miller frame 24 after miller frame 24 has been assembled into miller shell 26. As shown, representatively by two cutters 22 in FIG. 2, a family of cutters 22 are preferably provided to the surgeon with all members of the family having common sized bearing surfaces 56 and tips 60. In all cases, bearing surface 56 preferably has an outer diameter 110 which is larger than or equal to the outer diameter 111 of cutting surface 78. The cutter 22 also includes a head 80 having a drive tip receiver 112 formed therein for coupling to the distal tip 158 of the drive shaft assembly 122 for turning the cutter 22. The proximal end 146 of the drive shaft assembly 122 is coupled to a drive means (not shown) such as a drill. The drive means can be hand or power operated and advances with the cutter 22 as that means is moved into the bone by the surgeon through the use of strike plate 50 of miller frame 24.

As discussed above, miller frame 24 and miller shell 26 include indicators 28, 30. Indicators 30 comprises three indices corresponding to three different triangles, referred to as small ("SML"), large ("LRG"), and double extra large ("XXL") in the figures. More or less indices can be used as desired and, of course, can be otherwise designated. Illustratively, indicator 28 comprises the upper end of miller shell 26. However, it is within the scope of the disclosure for miller shell 26 to include other structures or indicia thereon acting as indicator 28 for alignment with indicators 28 of miller frame 24.

The operation of the indicators 28, 30 can be seen most clearly in FIG. 1. FIG. 1 shows the configuration of the instrument 20 with indicators 28 in alignment with the "SML" index of indicators 30. This corresponds to cutter 22 having progressed into the bone sufficiently far to accept a prosthesis having a "small" triangular-shaped projection (see for example, projection "A" of FIG. 2 of incorporated U.S. Pat. No. 5,540,694.) If this is the prosthesis which the surgeon wishes to use, the cutting process would be stopped at this point. However, if the surgeon wishes to use a prosthesis having a larger triangular-shaped projection, he or she would continue advancing the cutter 22 until either the "LRG" or "XXL" index 30 was aligned with reference surface 28.

Miller shell 26 can include indicia 82 which relate to the geometry of the neck of the femoral prosthesis which is to be implanted. As shown in FIG. 2, these indicia are referenced to the most proximal portion 84 of the great trochanter 86 of the patient's femur. The index which lines up with proximal portion 84 provides the surgeon with information regarding selecting the appropriate neck geometry for the femoral component. Additional notations can be included on miller shell 26 to indicate the sleeve cone sizes for which the miller shell 26 is appropriate (see reference numeral 88 in FIG. 1). A general reference number to the cone size can also be imprinted on the miller shell 26 (see reference numeral 90 in FIG. 1).

The overall procedure in which instrument 20 is used is as follows. First, an incision 18 large enough to receive the effective width of the miller frame 24 is made through which the patient's femur is prepared by cutting with a straight reamer to establish an extended cavity and center line for receipt of the distal stem of the femoral prosthesis. Second, the proximal femur is reamed with a conical reamer to form a cavity for receiving the conical portion of a sleeve or a stem of a prosthesis. This conical cavity is on the same center line as the straight cavity and the reaming is conducted until the proximal end of the reamer is even with the proximal end of the resected femur (see reference numeral 92 in FIG. 1).

Third, surgical instrument 20 in its assembled form as shown in FIG. 1 is inserted into the proximal end of the femur. The assembled instrument includes a cutter 22, a miller frame 24, miller shell 26, and a pilot shaft 42 which are appropriate to 1) the size of the triangular projection of the sleeve which the surgeon wishes to implant, and 2) the straight and conical cavities formed in the bone in steps 1 and 2.

Specifically, the diameter of cutter 22 is selected based on the width W of the triangular projection of the sleeve which is to be implanted (see FIG. 1 of incorporated U.S. Pat. No. 5,540,694). The miller shell 26 is selected based on the size of the conical reamer used in step 2. Specifically, conical portion 44 of miller shell 26 has the same taper and same maximum diameter as the conical reamer. The height of conical portion 44 is preferably slightly less than the height of the conical reamer so that the proximal end of the conical portion can be aligned with the resected end 92 of the femur without bottoming out in the reamed conical cavity. The pilot shaft 42 is selected based on the size of the straight reamer used in step 1 which in turn is selected by the surgeon based on the inside diameter of the patient's femur.

To provide the surgeon with the ability to match the finished prosthesis to various patient requirements, sleeves of various sizes and configurations and femoral prostheses having various proximal and distal diameters are provided to the surgeon along with corresponding sets of cutters 22, pilot shafts 42, miller shells 26, and straight and conical reamers. Preferably, only a single miller frame 24 is used in the overall system, such miller frame 24 being able to accept all cutters 22 and being receivable in all miller shells 26.

The initial insertion of instrument 20 into the cavity in the femur brings the proximal end of conical portion 44 into alignment with the proximal end 92 of the resected femur. At this point, the surgeon can use indicia 82 to confirm his or her selection of a neck geometry for the femoral prosthesis.

Cutter 22 is then rotated by the drive shaft assembly 122 coupled to the driving means (not shown) while miller frame 24 is moved along longitudinal axis 40 of miller shell 26. This process is continued until the appropriate index 30 on miller frame 24 is aligned with reference surface 28, e.g., until the "LRG" index is aligned if the sleeve to be inserted is to have a "LRG" triangular projection. In some cases, the original choice of triangular projection may be too small to reach the patient's hard bone at the proximal end of the femur, in which case the cutting of the triangular cavity would be continued to the next index mark and a further evaluation would be made at that point. If suitable at this point, a sleeve having a triangular portion corresponding to the index mark 30 to which the cutting was continued would be used. Depending upon the circumstances, all or portions of the process may be repeated until a suitable fit is achieved.

Instrument 20 is removed from the patient's femur by pulling miller frame 24 straight out using strike plate 50 while rotating the strike plate 50 to ensure the engagement of pin 72 with surface 74 of miller shell 26. A light tap on the strike plate 50 from below with a hand, mallet, or other instrument, is usually sufficient to release miller shell 26 from the patient's bone allowing complete removal of the instrument 20. Implantation of the femoral prosthesis then follows.

Instrument 20 is fabricated using conventional techniques used in the manufacture of surgical instruments. Similarly, the instrument 20, except for sleeve 124 is composed of conventional stainless steels or other materials employed in constructing surgical instruments. Illustratively, sleeve 124 is fabricated from a composite material such as Celcon or another suitable material.

Also, while shielded drive shaft assembly 120 has been shown oriented parallel to the shaft 48, it is within the scope of the disclosure for shielded drive shaft assembly to be oriented at other angle with respect to the shaft 48. Those skilled in the art will recognize that if the shielded drive shaft assembly slants inwardly (distally to proximally) that the full benefits of the reduction in incision length will be recognized. At such an angle, sleeve 124 could even be removed from drive shaft 1 assembly 22 within the scope of the disclosure. However, as the inwardly slant increases, those skilled in the art will recognize that the complexity of the coupling between the drive shaft 128 and the miller cutter 22 will likely increase resulting in a loss of the benefit of being able to use a simple pinned-sleeve shaft coupling. It is also within the scope of the disclosure for shielded drive shaft 120 or an unshielded drive shaft 128 to slant outwardly (distally to proximally) with respect to shaft 48. Those skilled in the art will recognize that as the outward slant increase and approaches a situation in which the driving force spins about the axis 113 of cutter 22, the amount the size of the incision 18 can be decreased gets smaller resulting in larger incisions 18. Also, the amount the size of the incision 18 can be decreased gets smaller resulting in larger incisions 18 as shielding is removed between the drive shaft 128 and soft tissue.

Although specific embodiments of the invention have been described herein, other embodiments may be perceived by those skilled in the art without departing from the scope of the invention as defined by the following claims. For example, although the invention has been described in terms of the implantation of the femoral portion of a hip prosthesis, it can be used with prostheses for other joints such as the shoulder, knee, or elbow.

What is claimed is:

1. A bone miller system comprising:
   a shell configured for insertion within a bone cavity and including a shaft cavity;
   a frame shaft configured for sliding reception into the shaft cavity along a longitudinal axis of the shaft cavity;
   at least one cutter defining a cutter axis, the at least one cutter including a first drive joint member;
   a cutter mount configured to support the at least one cutter such that the cutter axis intersects the longitudinal axis at a first angle;
   a drive shaft defining a drive shaft axis, the drive shaft including a proximal end configured to receive rotational force to rotate the drive shaft about the drive shaft axis, and a distal end with a second drive joint member, the second drive joint member configured to operably couple with the first drive joint member to rotate the at least one cutter about the cutter axis; and
   a shaft alignment bracket configured to support the drive shaft at a fixed angular relationship with respect to the frame shaft, such that the drive shaft axis intersects the cutter axis at a second angle, wherein the second angle is about equal to or greater than the first angle.

2. The bone miller system of claim 1, wherein the at least one cutter comprises a plurality of cutters, each of the plurality of cutters having a diameter different from the diameter of each of the other of the plurality of cutters.

3. The bone miller system of claim 1, wherein one of the first drive joint member and the second drive joint member comprises a pin and the other of the first drive joint member and the second drive joint member comprises a fork.

4. The bone miller system of claim 1, further comprising:
a sleeve;
a bore extending through the sleeve and configured to slidably and rotatably receive the drive shaft; and
a guide member for slidably guiding the sleeve with the shaft alignment bracket.

5. The bone miller system of claim 4, wherein:
the shaft alignment bracket includes an arm portion extending from the frame shaft to a receiver, the receiver sized to slidably support the drive shaft;
the bore is sized to slidably receive the receiver; and
the guide member comprises a slot having a diameter sized to receive the arm portion therethrough.

6. The bone miller system of claim 5, the sleeve further including:
a notch extending radially from the slot.

7. The bone miller system of claim 5, the shell further comprising:
a slot extending along the longitudinal axis and sized to slidably receive the arm portion.

8. The bone miller system of claim 1, wherein the cutter mount is fixedly supported by the frame shaft.

9. A bone miller system comprising:
a frame shaft defining a longitudinal axis;
at least one cutter defining a cutter axis, the at least one cutter including a first drive joint member;
a drive shaft defining a drive shaft axis, the drive shaft including a proximal end configured to receive rotational force to rotate the drive shaft about the drive shaft axis, and a distal end with a second drive joint member, the second drive joint member configured to operably couple with the first drive joint member to rotate the at least one cutter about the cutter axis; and
a bracket assembly configured to (i) support the at least one cutter such that the cutter axis intersects the longitudinal axis at a first angle, and (ii) support the drive shaft at a fixed angular relationship with respect to the frame shaft, wherein the drive shaft axis is about parallel to the longitudinal axis.

10. The system of claim 9, further comprising:
a shell configured for insertion within a bone cavity and including a shaft cavity configured for sliding reception of the frame shaft.

11. The system of claim 10, the shell further comprising:
a slot extending along the shell and sized to slidably receive a portion of the bracket assembly.

12. The system of claim 9, wherein:
the at least one cutter comprises a cutting surface having an outer diameter, and an end portion with a bearing surface having an outer diameter larger than the outer diameter of the cutting surface; and
the bracket assembly comprises a bearing surface for rotatably mating with the bearing surface of the cutter.

13. The system of claim 9, further comprising:
a sleeve;
a bore extending through the sleeve and configured to slidably and rotatably receive the drive shaft; and
a guide member for slidably guiding the sleeve with the bracket assembly.

14. The system of claim 13, wherein:
the bracket assembly includes an arm portion extending from the frame shaft to a receiver, the receiver sized to slidably support the drive shaft;
the bore is sized to slidably receive the receiver; and
the guide member comprises a slot having a diameter sized to receive the arm portion therethrough.

15. The system of claim 14, the sleeve further including:
a notch extending radially from the slot.

16. A bone miller system comprising:
a frame shaft defining a longitudinal axis;
a cutter mount fixedly attached to the frame shaft and defining a cutter mount axis that intersects the longitudinal axis at a first angle;
a shaft alignment bracket fixedly attached to the frame shaft and defining a drive axis, the drive axis substantially parallel to the longitudinal axis;
at least one cutter configured to rotate about the cutter mount axis when the at least one cutter is supported by the cutter mount; and
a drive shaft configured to rotate about the drive axis when the drive shaft is supported by the shaft alignment bracket, and configured to operably couple with the at least one cutter to rotate the at least one cutter about the cutter axis.

17. The system of claim 16, further comprising:
a shell configured for insertion within a bone cavity and including a shaft cavity configured for sliding reception of the frame shaft.

18. The system of claim 17, the shell further comprising:
a slot extending along the shell and sized to slidably receive a portion of the cutter mount.

19. The system of claim 16, wherein:
the at least one cutter comprises a cutting surface having an outer diameter, and an end portion with a bearing surface having an outer diameter larger than the outer diameter of the cutting surface; and
the cutter mount comprises a bearing surface for rotatably mating with the bearing surface of the cutter.

20. The system of claim 16, further comprising:
a sleeve;
a bore extending through the sleeve and configured to slidably and rotatably receive the drive shaft; and
a guide member for slidably guiding the sleeve with the shaft alignment bracket.

21. The system of claim 20, wherein:
the shaft alignment bracket includes an arm portion extending from the frame shaft to a receiver, the receiver sized to slidably support the drive shaft;
the bore is sized to slidably receive the receiver; and
the guide member comprises a slot having a diameter sized to receive the arm portion therethrough.

* * * * *